United States Patent
Attinger (12)

(10) Patent No.: US 11,350,812 B2
(45) Date of Patent: Jun. 7, 2022

(54) ENDOSCOPE SHAFT HAVING A LAYERED STRUCTURE, AND METHOD FOR PRODUCING SAME

(71) Applicant: KARL STORZ SE & Co. KG, Tuttlingen (DE)

(72) Inventor: Juerg Attinger, Stein am Rhein (CH)

(73) Assignee: KARL STORZ SE & Co. KG, Tuttlingen (DE)

(*) Notice: Subject to any disclaimer, the term of this patent is extended or adjusted under 35 U.S.C. 154(b) by 168 days.

(21) Appl. No.: 16/542,902

(22) Filed: Aug. 16, 2019

(65) Prior Publication Data
US 2020/0070482 A1    Mar. 5, 2020

(30) Foreign Application Priority Data
Aug. 30, 2018    (DE) ..................... 10 2018 121 206.2

(51) Int. Cl.
*A61B 1/00*     (2006.01)
*A61B 1/005*    (2006.01)
(Continued)

(52) U.S. Cl.
CPC .......... *A61B 1/00071* (2013.01); *A61B 1/005* (2013.01); *A61B 1/0011* (2013.01);
(Continued)

(58) Field of Classification Search
CPC . A61B 1/00064; A61B 1/00071; A61B 1/005; A61B 1/0051; A61B 1/0052;
(Continued)

(56) References Cited

U.S. PATENT DOCUMENTS 3,558,754 A * 1/1971 Martin .................... B32B 5/026
                                                    264/516
3,734,139 A * 5/1973 Zafiroglu ................ B29C 65/48
                                                    138/146
(Continued)

FOREIGN PATENT DOCUMENTS

DE        10122203 A1    1/2002
DE        4438944 C2    10/2003
(Continued)

OTHER PUBLICATIONS

German Search Report (Including Translation) for German Patent Application No. 10 2018 121 206.2, dated Jul. 1, 2019.
(Continued)

*Primary Examiner* — Ryan N Henderson
(74) *Attorney, Agent, or Firm* — Jason H. Vick; Sheridan Ross, PC

(57) ABSTRACT

The invention relates to an endoscope shaft 1 having a layered structure. In this shaft 1, formed as a curved or non-curved hollow cylinder, various layers succeed and enclose one another radially over the entire length or a substantial part of the length of the shaft. The shaft has an inner layer 2 of plastic, and an outer layer 3 of plastic enclosing the inner layer 2, and a structuring layer 4 in the transition region 5 of the inner layer and the outer layer 3. The plastics of the inner layer and of the outer layer 3 are different, and the inner layer and the outer layer 3 mesh together in the transition region 5. Thus, the inner layer and the outer layer 3 can connect to each other particularly well, and a delamination of the inner layer and of the outer layer 3 can thus be prevented. This is specifically because the interface between the inner layer and the outer layer 3 is enlarged, in relation to the prior art, by the mutual meshing 6. Moreover, the geometry of the mutual meshing creates a particularly stable and durable mechanical connection
(Continued)

Figure 1:
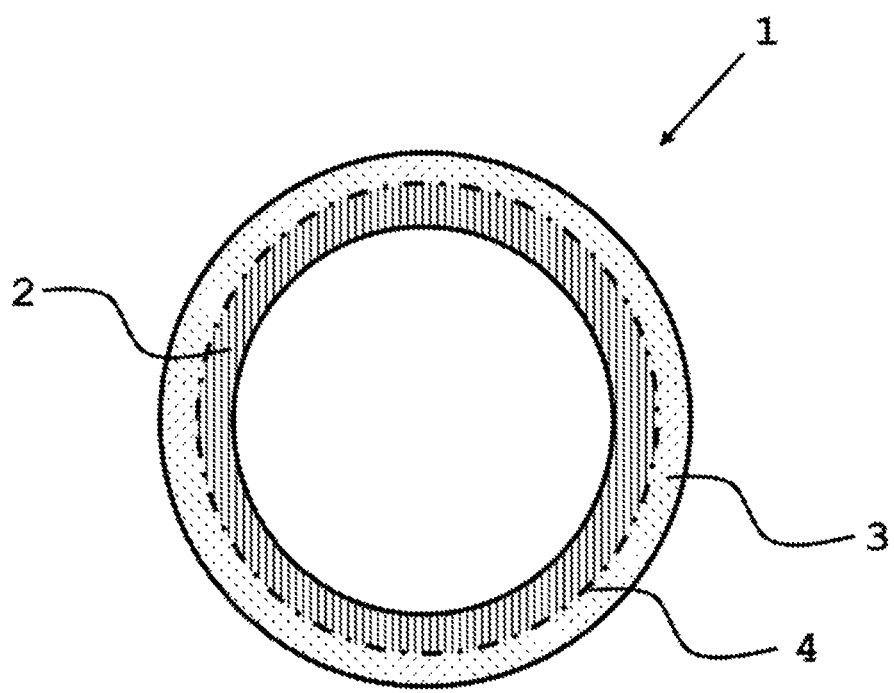

between the layers 2, 3 and 4, which allows forces to be transmitted from one of the layers 2, 3, 4 to another in a particularly reliable and permanent manner, as a result of which undesired delamination is prevented, in particular in flexible endoscope shafts 1.

The invention further relates to a method for producing such an endoscope shaft 1 according to the invention.

14 Claims, 3 Drawing Sheets

(51) Int. Cl.
| | |
|---|---|
| A61L 29/04 | (2006.01) |
| B32B 27/08 | (2006.01) |
| B32B 27/12 | (2006.01) |
| B32B 27/28 | (2006.01) |
| B32B 27/36 | (2006.01) |
| B32B 5/02 | (2006.01) |

(52) U.S. Cl.
CPC ............ *A61B 1/0055* (2013.01); *A61L 29/04* (2013.01); *B32B 27/08* (2013.01); *B32B 27/12* (2013.01); *B32B 27/28* (2013.01); *B32B 27/36* (2013.01); *B32B 5/024* (2013.01); *B32B 2535/00* (2013.01)

(58) Field of Classification Search
CPC ... A61B 1/0053; A61B 1/0055; A61B 1/0056; A61M 25/0012; A61M 25/0021; A61M 2025/0046; A61M 2025/0047; A61M 2025/0048; A61L 29/04; B32B 27/08; B32B 27/12; B32B 27/28; B32B 27/36; B32B 5/024; B32B 2535/00

See application file for complete search history.

(56) References Cited

U.S. PATENT DOCUMENTS

| | | | | |
|---|---|---|---|---|
| 4,805,595 A * | 2/1989 | Kanbara | ............ | A61B 1/00071 600/140 |
| 5,529,820 A * | 6/1996 | Nomi | ............ | A61L 29/041 428/36.4 |
| 5,554,120 A * | 9/1996 | Chen | ............ | A61L 29/049 525/166 |
| 5,683,348 A | 11/1997 | Diener | | |
| 6,206,824 B1 * | 3/2001 | Ohara | ............ | A61B 1/00071 600/139 |
| 6,458,075 B1 * | 10/2002 | Sugiyama | ............ | A61B 1/00071 600/139 |
| 6,503,193 B1 * | 1/2003 | Iwasaki | ............ | A61B 1/00071 600/139 |
| 6,520,214 B1 * | 2/2003 | Sugiyama | ............ | A61B 1/00071 138/119 |
| 6,540,669 B2 * | 4/2003 | Abe | ............ | A61B 1/0055 600/139 |
| 6,623,424 B2 * | 9/2003 | Hayakawa | ............ | A61B 1/00071 600/139 |
| 6,860,849 B2 * | 3/2005 | Matsushita | ............ | A61B 1/00071 600/140 |
| 6,991,603 B2 * | 1/2006 | Krupa | ............ | A61B 1/0011 600/141 |
| 7,011,627 B2 * | 3/2006 | Abe | ............ | A61B 1/0055 600/139 |
| 7,044,906 B2 * | 5/2006 | Hosoi | ............ | A61B 1/005 600/139 |
| 7,789,827 B2 | 9/2010 | Landry | | |
| 8,905,921 B2 * | 12/2014 | Titus | ............ | A61B 1/00137 600/175 |
| 9,044,139 B2 * | 6/2015 | Takahashi | ............ | A61B 1/00078 |
| 9,629,978 B2 * | 4/2017 | Eversull | ............ | A61M 25/0045 |
| 10,130,790 B2 * | 11/2018 | Otake | ............ | A61M 25/005 |
| 10,722,682 B2 * | 7/2020 | Kubo | ............ | A61M 25/005 |
| 2002/0010386 A1 * | 1/2002 | Matsushita | ............ | A61L 29/085 600/140 |
| 2002/0028984 A1 * | 3/2002 | Hayakawa | ............ | A61B 1/005 600/139 |
| 2003/0216616 A1 * | 11/2003 | Krupa | ............ | A61B 1/0055 600/140 |
| 2003/0220543 A1 * | 11/2003 | Abe | ............ | A61B 1/0055 600/140 |
| 2005/0020881 A1 * | 1/2005 | Hosoi | ............ | C08L 53/025 600/140 |
| 2005/0020882 A1 * | 1/2005 | Hosoi | ............ | A61B 1/005 600/140 |
| 2005/0061381 A1 * | 3/2005 | Hosoi | ............ | A61L 29/041 138/137 |
| 2005/0171591 A1 * | 8/2005 | McHale | ............ | A61M 25/0068 623/1.11 |
| 2008/0091169 A1 * | 4/2008 | Heideman | ............ | A61M 25/01 604/527 |
| 2008/0300462 A1 | 12/2008 | Intoccia et al. | | |
| 2009/0165881 A1 * | 7/2009 | Tegg | ............ | A61M 25/005 138/137 |
| 2009/0166913 A1 * | 7/2009 | Guo | ............ | B29C 48/151 264/171.27 |
| 2009/0171319 A1 * | 7/2009 | Guo | ............ | A61M 25/0043 604/526 |
| 2010/0036201 A1 | 2/2010 | Ogura | | |
| 2010/0217257 A1 * | 8/2010 | Howat | ............ | A61B 18/1492 606/34 |
| 2012/0071722 A1 * | 3/2012 | Nakamura | ............ | A61B 1/00078 600/140 |
| 2012/0097194 A1 * | 4/2012 | McDaniel | ............ | C09D 7/65 134/26 |
| 2012/0180896 A1 * | 7/2012 | Takahashi | ............ | A61B 1/00078 138/137 |
| 2015/0032104 A1 * | 1/2015 | Howat | ............ | A61B 5/6852 606/41 |
| 2016/0136387 A1 * | 5/2016 | Otake | ............ | A61M 25/0045 604/526 |
| 2017/0079546 A1 * | 3/2017 | Costello | ............ | A61B 5/062 |
| 2018/0185610 A1 * | 7/2018 | Tegg | ............ | B29C 63/0069 |
| 2018/0310957 A1 * | 11/2018 | Cise | ............ | A61M 25/001 |
| 2019/0224446 A1 * | 7/2019 | Ranum | ............ | A61B 5/6852 |
| 2019/0224447 A1 * | 7/2019 | Ranum | ............ | B21F 15/04 |
| 2020/0155805 A1 * | 5/2020 | Sugawara | ............ | A61M 25/0053 |
| 2020/0324077 A1 * | 10/2020 | Knutson | ............ | A61M 25/0105 |
| 2020/0406025 A1 * | 12/2020 | Guo | ............ | A61M 25/0668 |
| 2021/0045644 A1 * | 2/2021 | Kramer | ............ | A61N 1/056 |
| 2021/0213243 A1 * | 7/2021 | Guo | ............ | A61M 25/0021 |
| 2021/0386968 A1 * | 12/2021 | Guo | ............ | A61L 29/14 |

FOREIGN PATENT DOCUMENTS

| | | |
|---|---|---|
| EP | 2382002 A1 | 11/2011 |
| EP | 1891881 B1 | 4/2014 |

OTHER PUBLICATIONS

European Search Report for corresponding European Application No. 19190241.0, dated Jan. 27, 2020.

German Search Report for German Patent Application No. 10 2018 121 206.2, dated Jul. 1, 2019.

* cited by examiner

ENDOSCOPE SHAFT HAVING A LAYERED STRUCTURE, AND METHOD FOR PRODUCING SAME

Cross Reference to Related Applications

This application claims the benefit under 35 U.S.C. 119(a) to German Patent Application No. 10 2018 121 206.2, filed Aug. 30, 2018, the disclosure of which is incorporated herein by reference in its entirety.

TECHNICAL FIELD

The invention relates to an endoscope shaft having a layered structure, and to a method for producing same.

PRIOR ART

An endoscope that is flexible at least in part, and has an endoscope shaft with a layered structure, is known from the German patent DE 44 38 944 C2. It has a tubular shaft made of a nickel-titanium alloy and, arranged in the latter, a rigid tube section with an objective arranged therein, wherein an optical waveguide is arranged between the tubular shaft and the rigid tube section. This endoscope shaft has a complicated design with a series of components which are separate from one another and which have to be laboriously coordinated with one another in order to ensure a reliable and durable structure of the endoscope shaft.

An endoscope shaft with variable flexibility is known from the European patent EP 1 891 881 B1. The shaft has a flexible outer layer and an inner layer, wherein the inner layer has a latticework for stabilization, and the flexible outer layer has expansion elements which, controlled by the user, can change their longitudinal extent and can thus bring about a change of the curvature of the flexible outer layer, in relation to the inner layer, and therefore of the endoscope shaft. After prolonged use and strong bending stresses, these endoscope shafts run the risk of delamination and therefore loss of the controlled adjustment of the curvature of the endoscope shaft.

DESCRIPTION OF THE INVENTION

The object of the invention is to make available a shaft for an endoscope, said shaft being improved in relation to the prior art and being distinguished by particular durability. A further object is to make available a method for producing such an endoscope shaft having a layered structure.

One object is achieved according to the invention by an endoscope shaft having a layered structure and having the features set forth in claim 1. The other object for producing the invention is achieved by a method that has the features set forth in claim 10.

Advantageous embodiments of the invention are the subject matter of the dependent claims.

The endoscope shaft according to the invention has a layered structure in which, in the manner of a curved or non-curved hollow cylinder, various layers succeed one another radially over the entire length or at least over a substantial part of the length of the shaft and enclose each other layer by layer. The shaft with said layered structure has at least one inner layer of plastic, and an outer layer of plastic enclosing the inner layer, and a structuring layer in the transition region of the inner layer and the outer layer. According to the invention, the chosen plastics of the inner layer and of the outer layer are different, and the inner layer and the outer layer are designed meshing together in the transition region. It is thus possible for the inner layer and the outer layer to be connected to each other particularly well, thereby preventing a delamination of the inner layer and of the outer layer. According to the invention, this is achieved by the fact that the interface between the inner layer and the outer layer is enlarged, in relation to the prior art, as a result of the meshing together, and furthermore the geometry of the meshing together creates a particularly stable and durable mechanical connection between the layers, which allows forces to be transmitted from one of the layers to another in a particularly reliable and permanent manner, as a result of which the undesired delamination is prevented. This proves very important specifically in flexible endoscope shafts.

In a particularly preferred embodiment of the endoscope shaft according to the invention, the plastic of the inner layer has a melting point that is lower, particularly at least 20° C. lower or preferably at least 30° C. lower, than the melting point of the plastic of the outer layer. When applying the outer layer for example by coextrusion onto the inner layer, it is thus possible for the inner layer to be made to melt and for these two molten layers to melt into each other, without the plastics of the two layers altering chemically. Alternatively or in addition, the melting of the two layers in the transition region can be obtained by introducing additional energy, for example by irradiation by means of infrared radiation, ultrasound or application of electrical energy, in particular by alternating fields. Through the melting together of the inner layer and outer layer made of the different plastics, the desired meshing of the two layers is achieved in a particularly simple manner, which brings about the desired durability of the two layers and therefore of the endoscope shaft.

It has proven particularly advantageous to choose the plastic of the inner layer such that its melting point is at least 20° C. lower or preferably at least 30° C. lower that that of the plastic of the outer layer. The desired melting together of the inner layer and the outer layer can be achieved particularly reliably by virtue of this marked difference in melting point.

In a particularly preferred embodiment of the endoscope shaft according to the invention, the plastic of the outer layer of the endoscope shaft according to the invention is chosen as polyether block amide block copolymer, in particular as PEBAX, and/or as glycol-modified polycyclohexylene dimethylene terephthalate (PCTG). These plastics prove particularly suitable for use as the main constituent of a flexible endoscope shaft, in particular the outer layer of the endoscope shaft. This is especially due to the durability of these plastics both in terms of mechanical properties and also chemical and biochemical properties and as regards long-term stability. These specific plastics, in particular PEBAX and glycol-modified polycyclohexylene dimethylene terephthalate (PCTG), permit in particular the medical use in a flexible endoscope in conjunction with a connected inner layer formed according to the invention.

For this inner layer of the endoscope shaft according to the invention, one or more plastics are preferably chosen from among polyurethane (PU), thermoplastic polyurethane (TPU) and/or from styrene block copolymer, in particular styrene-ethylene-butylene-styrene (SEBS). On the one hand, by virtue of their respective melting points, these plastics prove to be suitable partners to the aforementioned particularly preferred plastics for the outer layer, and, on the other hand, by virtue of their durability and simple handling, they prove particularly suitable for the inner layer, in which elements are regularly introduced for increasing the mechanical stability and/or for deformation and/or for modifying the length and/or elements for monitoring the properties (temperature, stress, position and the like). The combinations of plastics that have proven particularly suitable for the inner layer and the outer layer are those of PEBAX and polyurethane (PU) and, respectively, glycol-modified polycyclohexylene dimethylene terephthalate (PCTG) and styrene-ethylene-butylene-styrene (SEBS).

According to a preferred development of the endoscope shaft according to the invention, the structuring layer is provided with a multiplicity of holes, which are separated from one another by webs. According to the invention, at least a plastic of the inner layer and/or of the outer layer protrudes through these holes and forms at least part of the meshed configuration of inner layer and outer layer. By way of its holes and webs, this structuring layer makes it possible to control the extent of the meshing of the inner layer and outer layer.

This is also achieved in particular through the positioning of the structuring layer in the transition region between the inner layer and the outer layer. In particular, the structuring layer can form a boundary of the transition region, if exclusively a plastic from one side of the layer in question extends through the holes in the direction of the other layer and meshes into the latter. This preferably takes place in the inner layer, such that the latter with its structuring properties protects in particular the cavity in the endoscope shaft, whereas, specifically in the case of flexible endoscopes, elements for changing the shape, in particular the curvature, or for sensing the properties of the endoscope or of the environment can be introduced and can particularly advantageously fulfil their function there on account of the proximity to the body.

It has proven particularly advantageous to form the structuring layer substantially from metal and/or plastic, in particular from metal wires and/or plastic fibers, or from a perforated woven fabric of plastic fibers and/or metal wires. It has proven particularly expedient here to choose structured films of plastic (in particular of polyethylene (PE), polypropylene (PP), polytetrafluoroethylene (PTFE, Teflon), polystyrene (PS), polycarbonate (PC) or polyvinylidene fluoride (PVDF)) or of metal (in particular of steel, medical steels, aluminum, titanium) or of hybrid materials with plastic or metal, which, by suitable selection of the material thickness, the materials or the frequency, position and formation of the holes (in particular round, oval, angular, extending preferentially in the longitudinal direction of the endoscope shaft), can fulfil in particular the requirements of a structuring element for a structuring layer of an endoscope shaft according to the invention.

Besides these films, structures made of metal wires and/or plastic fibers, in particular as a perforated woven fabric of plastic fibers and/or metal wires, have also proven suitable. The woven fabrics specifically make it possible to choose precisely and to optimize the properties of the structuring layer particularly as regards the arrangement and configuration of the holes for the passage of a plastic in order to provide the meshing together, without substantially ignoring the structuring importance for the endoscope shaft. A structuring layer made of a braided weave with regularly arranged holes, in particular of stainless steel filaments or plastic fibers, in particular of polyethylene (PE), polypropylene (PP), polyamide (PA, Nylon), polyvinyl chloride (PVC), polyphenylene terephthalamide (PPTA, Kevlar), has proven particularly advantageous.

The holes of the structuring layer preferably have a size of over 0.1 mm, preferably 0.2 mm, particularly 0.5 mm or 1 mm, and webs of the structuring layer in particular have a width of over 0.1 mm, preferably 0.2 mm or else over 0.5 mm. This choice particularly reliably ensures the passage and meshing together of the different plastics and, specifically when using a braided weave as structuring layer, makes it possible to keep down the weight of the endoscope shaft, without substantially impairing the durability and the stability of the endoscope shaft. It has proven particularly expedient to choose the ratio between the size of the webs and the size of the holes in the region of or less than 0.5. The holes and also the webs have to be adapted, in particular in terms of their respective sizes, to the viscosity of the two materials of the inner layer and the outer layer and also of their mixture.

Furthermore, it has proven particularly advantageous for the inner layer and the outer layer to be designed meshing together in the transition region in a meandering fashion. This is achieved in particular by the fact that both plastics are liquefied in the transition region such that they mesh together in an alternating, meandering fashion and thereby form a very greatly enlarged mutual interface, which plastics, after cooling down, therefore provide a very high degree of mutual adhesion and in addition, by virtue of meshing together in a meandering fashion, largely exclude a mutual displacement and therefore separation (delamination) and thus also permit particular durability over a long period of time.

In a preferred development of the endoscope shaft according to the invention, the outer layer is enclosed by at least one external layer and/or the inner layer is designed such that it encloses at least one internal layer. These additional layers are provided in order to improve the surface properties of the endoscope shaft, whether on the outside and thus facing a body into which the endoscope shaft is introduced, or facing the cavity which is arranged in the interior of the endoscope shaft and which is used for the introduction of endoscopic tools into the body. The external layers are chosen and applied in particular to optimize the sliding properties with a low index of friction and to ensure the sterile and/or biocompatible properties of the endoscope, whereas the internal layers are chosen in particular to be mechanically robust. By virtue of these thin additional external and internal layers, the properties of the endoscope shaft according to the invention can be further improved specifically with respect to durability and usability.

In addition to the endoscope shaft according to the invention, the invention also relates to a method for producing an endoscope shaft having a layered structure. For this purpose, in a first step, an inner layer is formed from a first plastic and typically has the shape of a hollow cylinder. The hollow cylinder can have a circular cross section, but it can also have another closed cross section, in particular an oval cross section. According to the invention, this inner layer is provided with a structuring layer by a process in which a structuring layer is applied on the outer surface of the inner layer or a structuring layer is introduced in the region of the outer surface of the inner layer, and then an outer layer of a second plastic is applied on the outside of the inner layer with the structuring layer, said second plastic having a higher melting point than the first plastic. According to the invention, this is carried out such that the inner layer and the outer layer flow into each other and a meshing together of the two layers is thus obtained, as a result of which, after hardening, a very durable and firm connection of the inner layer to the outer layer is created. According to the invention, this is permitted specifically by the use of the different plastics with the different melting points, since, when the outer layer is applied in the molten state, the inner layer melts too according to the invention, thereby permitting the inventive meshing together of the two layers. A delamination of the two layers can thereby be largely excluded, since the production process according to the invention ensures that the adhesion forces between the inner layer and the outer layer are greatly increased by the enlargement of the interface between the two layers and, by virtue of the modified geometry of the interface caused by the meshing together of the two layers, a separation of the layers is made considerably difficult. It is thus possible to increase the durability of the endoscope shaft produced according to the invention.

In an advantageous development of the method according to the invention, provision is made that, during or after the application of the outer layer, the inner layer and the outer layer are heated in particular by infrared radiation and/or ultrasound. Through the additional introduction of thermal energy, it is possible to specifically guide and efficiently control the process of meshing together of the inner layer and outer layer, such that the plastics of the inner layer and of the outer layer do not suffer damage and mesh together well, the interface is effectively enlarged, and the adhesion forces between the two layers can therefore be greatly increased. The heating is in particular limited in location to the transition region between the two layers, i.e. the inner layer and the outer layer, such that these two layers flow into each other reliably and in a spatially limited manner and are thus able to mesh together.

In a preferred development of the method according to the invention for producing an endoscope shaft having a layered structure, the inner layer is formed by coextrusion onto a removable core. The specific use of the coextrusion method for forming the inner layer makes it possible to form the inner layer very precisely on the core in the manner of a hollow cylinder, as a result of which the conditions are readily obtained for a connection to the outer layer that is later to be applied in order to form the meshed arrangement. For the inner layer of the endoscope shaft according to the invention, one or more plastics are preferably chosen from polyurethane (PU), thermoplastic polyurethane (TPU) and/ or from styrene block copolymer, in particular styreneethylene-butylene-styrene (SEBS).

Furthermore, a particularly advantageous method for producing an endoscope shaft having a layered structure has proven to be one in which the structuring layer is formed by braiding, in which method a latticework with many holes is applied on the outer surface or in the region of the outer surface of the inner layer. The configuration of the structuring layer as a latticework for integration in the transition region between the inner layer and the outer layer of the endoscope shaft proves to be a very advantageous compromise between stability, flexibility and weight, which is particularly relevant as regards use in flexible endoscopes. A structuring layer made of a braided weave with regularly arranged holes, in particular of stainless steel filaments or plastic fibers, in particular of polyethylene (PE), polypropylene (PP), polyamide (PA, Nylon), polyvinyl chloride (PVC), polyphenylene terephthalamide (PPTA, Kevlar), has proven particularly advantageous.

In a particularly advantageous development of a method according to the invention for producing an endoscope shaft having a layered structure, the outer layer is applied to the inner layer with the structuring layer by coextrusion, at a processing temperature higher than the melting point of the inner layer. A meshing of the molten inner layer with the outer layer is thereby permitted which according to the invention permits a very secure and permanent connection of the inner layer and outer layer of the endoscope shaft and thus ensures excellent durability. The specific use of the coextrusion method for forming the outer layer on the inner layer with the structuring layer makes it possible to connect the inner layer to the outer layer such that both reliably mesh together in the liquid state. In this particularly preferred embodiment of the invention, the plastic of the outer layer is chosen as polyether block amide block copolymer, in particular as PEBAX, and/or as glycol-modified polycyclohexylene dimethylene terephthalate (PCTG).

The combinations of plastics that have proven particularly suitable for the inner layer and the outer layer are those of PEBAX and polyurethane (PU) and, respectively, polycyclohexylene dimethylene terephthalate (PCTG) and styreneethylene-butylene-styrene (SEBS). These combinations of plastics allow the two layers to readily flow into each other and thus mesh together upon application of the outer layer, which leads to melting of the inner layer. They also permit a good adhesive connection between the two meshed layers, which results in a particularly durable endoscope shaft being produced by the method according to the invention.

In a particularly preferred method according to the invention for producing a endoscope shaft having a layered structure, at least one external layer is applied in order to improve the sliding properties. This permits better handling of the shaft and less strain on the latter, which leads to better durability of the endoscope shaft produced.

The invention is explained in more detail below on the basis of preferred illustrative embodiments and by reference to the figures. The invention is not limited to these preferred illustrative embodiments.

Figure 2:
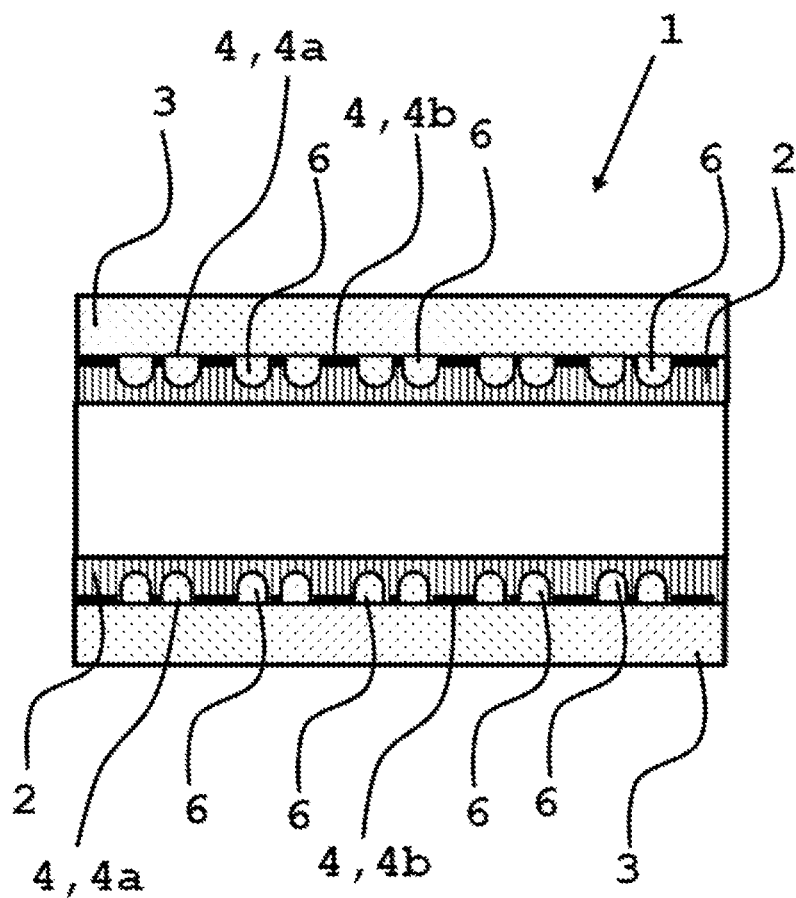
Figure 3:
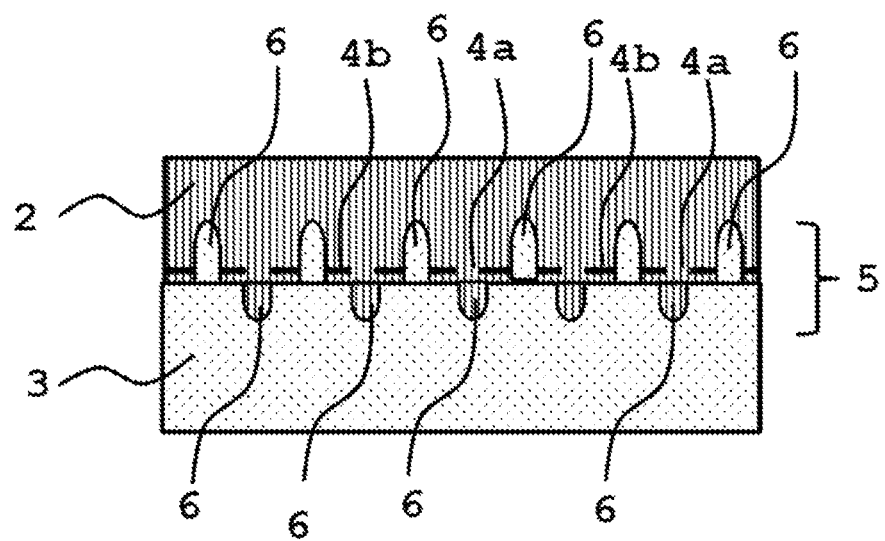

In the drawings:

FIG. 1 shows a schematic cross-sectional view of an example of an endoscope shaft according to the invention, FIG. 2 shows a schematic longitudinal section through an example of an endoscope shaft according to the invention, and FIG. 3 shows a schematic view of a detail of an example of an endoscope shaft.

FIG. 1 shows a schematic cross-sectional view of an example of a flexible endoscope shaft 1 according to the invention. The endoscope shaft 1 according to the invention is configured in the manner of a curved or non-curved hollow cylinder in which various layers succeed one another radially over the entire length of the shaft and enclose on another layer by layer. The shaft with this layered structure has an inner layer 2 of one plastic, and an outer layer 3 of another plastic enclosing the inner layer 2, and a structuring layer 4 in the transition region 5 between the inner layer 2 and the outer layer 3. According to the invention, the plastics of the inner layer 2 and of the outer layer 3 are different, and the inner layer 2 and the outer layer 3 are designed meshing with each other in the transition region 5. This meshing is not shown in FIG. 1. The meshing has the effect that the inner layer 2 and the outer layer 3 connect to each other particularly well, and a delamination of the inner layer 2 and of the outer layer 3 is thus prevented. According to the invention, this is achieved by the fact that the interface between the inner layer 2 and the outer layer 3 is enlarged, in relation to the prior art, as a result of the meshed arrangement 6, and, furthermore, the geometry of the meshed arrangement creates a particularly stable and durable mechanical connection between the layers 2, 3, which allows forces to be transmitted from one layer 2, 3 to the other layer 3, 2 in a particularly reliable and permanent manner, as a result of which undesired delamination is prevented. This proves particularly important specifically in flexible endoscope shafts.

The structuring layer 4 is arranged in the transition region 5 between the inner layer 2 and the outer layer 3 and, in the manner of a closed ring, encloses the inner layer 2, which is in turn enclosed together with the structuring layer 4 by the outer layer 3 in the manner of a closed ring.

The structuring layer 4 has a multiplicity of holes 4 which are separated from one another by webs. A plastic of the inner layer 2 or of the outer layer 3 can pass through the holes and into the other layer, flow into the outer layer 3 or into the inner layer 2 and thus bring about a meshing of the two layers 2, 3. This meshing results in a very robust, durable and firm connection of the inner layer 2 and of the outer layer 3 and also of the structuring layer 4.

FIG. 2 shows a schematic longitudinal section through an example of an endoscope shaft 1 according to the invention from FIG. 1. The structuring layer 4 has a plurality of holes 4a which are arranged regularly, but with different spacings from one another, over the length and the circumference of the structuring layer 4. The holes 4a are separated from one another by webs 4b which are of differing width. The structuring layer 4 forms a border between the inner layer 2 and the outer layer 3, wherein plastic of the outer layer 3 has passed through the holes 4a into the inner layer 2 and, in this way, bulges of the outer layer 3 into the inner layer 2 have formed, which produce the meshing arrangement 6 in the inner layer 2. By means of said meshing arrangement 6, the surface between the inner layer 2 and the outer layer 3 has become larger and in this way the force between the two layers is increased by the adhesion force acting between them. The action produced by the modified, meshed geometry of the layers contributes to this effect, and therefore a particularly stable and strong connection of the inner layer 2 and of the outer layer 3 is provided.

The structuring layer 4 is configured here as a perforated woven fabric of metal wires. The woven fabric specifically makes it possible to choose precisely and to optimize the properties of the structuring layer 4 particularly as regards the arrangement and configuration of the holes 4a for the passage of a plastic in order to provide the meshing arrangement, without substantially ignoring the structuring importance for the endoscope shaft. A structuring layer 4 made of a braided weave with regularly arranged holes 4a, in particular of stainless steel filaments, has proven particularly advantageous.

The circular holes 4a of the structuring layer 4 have a size of over 0.1 mm, preferably 0.2 mm, particularly 0.5 mm or 1 mm, and the webs 4b of the structuring layer 4 have a width of approximately 0.1 mm, preferably 0.2 mm or else over 0.5 mm. This choice ensures the passage and meshing together of the various plastics and, specifically when using a braided woven fabric as structuring layer 4, makes it possible to keep down the weight of the endoscope shaft 1, without substantially impairing the durability and the stability of the endoscope shaft 1. It has proven particularly expedient to choose the ratio between the size of the webs 4b and the size of the holes 4a in the region of 0.5.

In this configuration of the endoscope shaft 1 according to the invention, PEBAX is chosen as plastic for the outer layer 3 of the endoscope shaft 1 according to the invention. This plastic proves particularly suitable for use as the main constituent of a flexible endoscope shaft 1, in particular the outer layer 3 of the endoscope shaft 1. This is especially due to the strength of this plastic both in terms of mechanical properties and also chemical and biochemical properties and as regards long-term stability. This specific plastic PEBAX permits in particular the medical use in a flexible endoscope in conjunction with a connected inner layer 2 formed according to the invention, since it is approved for medical products and is additionally distinguished by a low index of kinetic friction.

Polyurethane (PU) is chosen as plastic for this inner layer 2 of the endoscope shaft 1 shown in FIG. 2. The latter plastic, because of its melting point, proves a suitable partner to the aforementioned plastic PEBAX for the outer layer 3. It has a melting point that is lower by more than 20°, or preferably 30°, than that of the PEBAX chosen for the outer layer 3. Moreover, by virtue of its strength and simple handling, it proves particularly suitable for the inner layer 2, into which are introduced elements for increasing the mechanical stability and/of for deformation and/or for modifying the length and/or elements for monitoring the properties (temperature, stress, position and the like).

Specifically this combination of plastics for the inner layer 2 and the outer layer 3 proves particularly advantageous since it is possible to create the meshing 6 according to the invention in the context of applying the outer layer 3 to the composite of inner layer 2 and structuring layer 4 by coextrusion, which takes place at a temperature in the region of the melting point of PEBAX, since at this working temperature the inner layer of PU melts too, such that the different plastics can flow into each other, resulting in a meshing together of the two layers 2, 3.

FIG. 3 shows a schematic detail of another example of an endoscope shaft 1. It shows the inner layer 2, which is adjoined by the outer layer 3.

In the inner layer 2, spaced apart from the outer layer 3, the structuring layer 4, which is formed by a structured film of the plastic polyvinylidene fluoride (PVDF), extends over the length and the circumference of the inner layer 2. The material thickness, the frequency, the position and the formation of the holes is chosen in such a way as to achieve a sufficient stability, the lowest possible weight and a good meshing of the plastics of the inner layer 2 and of the outer layer 3 for the endoscope shaft 1 according to the invention.

In this configuration of this endoscope shaft 1 according to the invention, the chosen plastic for the outer layer 3 of the endoscope shaft 1 according to the invention is glycol-modified polycyclohexylene dimethylene terephthalate (PCTG). The plastic chosen for the inner layer 2 of this endoscope shaft 1 shown in FIG. 3 is styrene-ethylene-butylene-styrene (SEBS). The latter, with its melting point in the range between 150° C. and 210° C., proves a suitable partner to the aforementioned plastic glycol-modified polycyclohexylene dimethylene terephthalate (PCTG) with a melting point or processing temperature of approximately 240° C. Styrene-ethylene-butylene-styrene (SEBS), by virtue of its durability and simple handling, also proves particularly suitable for the inner layer 2. In particular, it proves especially suitable for receiving the aforementioned structured plastic film as structured layer 4 by encapsulation by means of coextrusion.

When applying the outer layer 3 to the inner layer 2, the inner layer 2 melts at the surface, as a result of which bulges form which are directed from the inner layer 2 to the outer layer 3, and also conversely from the outer layer 3 to the inner layer 2, and which create the meshing 6. Individual meshes 6 also extend through the holes 4a of the structuring layer 4.

Through the meshing of one layer 2, 3 with the other layer 3, 2, a meandering structure of meshes 6 is obtained which is distinguished by excellent durability and a firm connection of the layers 2, 3, 4 involved. The undesired delamination of the inner layer 2 and of the outer layer 3 is thus largely excluded. FIG. 3 moreover shows the transition region 5 between the inner layer 2 and the outer layer 3. The transition region 5 extends from the widest extent of the bulge of the inner layer 2 into the outer layer 3 (meshing 6) to the widest extent of the bulge of the outer layer 3 into the inner layer 2 (meshing 6). The structuring layer 4 is located in this transition region 5.

The invention relates to an endoscope shaft 1 having a layered structure. In this shaft designed as a curved or non-curved hollow cylinder, various layers succeed and enclose one another radially over the entire length or a substantial part of the length of the shaft. The shaft has an inner layer 2 of plastic, and an outer layer 3 of plastic enclosing the inner layer 2, and a structuring layer 4 in the transition region 5 between the inner layer and the outer layer 3. The plastics of the inner layer and of the outer layer 3 are different, and the inner layer and the outer layer 3 mesh with each other in the transition region 5. Thus, the inner layer and the outer layer 3 can connect to each other particularly well, and a delamination of the inner layer and of the outer layer 3 can thus be prevented. This is specifically because the interface between the inner layer and the outer layer 3 is enlarged, in relation to the prior art, by the meshing arrangement 6. Moreover, the geometry of the meshing arrangement creates a particularly stable and durable mechanical connection between the layers 2, 3 and 4, which allows forces to be transmitted from one of the layers 2, 3, 4 to another in a particularly reliable and permanent manner, as a result of which undesired delamination is prevented, particularly in flexible endoscope shafts 1.

The invention further relates to a method for producing such an endoscope shaft 1 according to the invention.

LIST OF REFERENCE SIGNS

1 endoscope shaft
2 inner layer
3 outer layer
4 structuring layer
4a holes
4b webs
5 transition region between inner and outer layer
6 meshing

The invention claimed is:

1. An endoscope shaft comprising:
a layered structure comprising an inner layer of plastic, an outer layer of plastic enclosing the inner layer, and
a structuring layer, formed substantially from metal and/or plastic, in a transition region of the inner layer and the outer layer, wherein the plastics for the inner layer and for the outer layer are different, and, after a coextrusion, the inner layer and the outer layer mesh together in the transition region to enlarge the surface between the inner layer and the outer layer, the structuring layer including a woven fabric with a multiplicity of holes over a length and circumference of the structuring layer separated by webs of varying width through which bulges of the inner layer, made from the inner layer of plastic, protrude into the outer layer and/or bulges of the outer layer, made from the outer layer of plastic, protrude into the inner layer, wherein the plastic of the inner layer has a melting point that is at least 20° C. lower than the melting point of the plastic of the outer layer.

2. The endoscope shaft according to claim 1, wherein the plastic of the outer layer is a polyether block amide block copolymer (PEBAX) and the plastic of the inner layer is a polyurethane (PU), a thermoplastic polyurethane (TPU), a styrene block copolymer, and/or a styrene-ethylene-butylene-styrene (SEBS).

3. The endoscope shaft according to claim 1, wherein the structuring layer has the multiplicity of holes which are separated from one another by the webs and through which at least a plastic of the inner layer and/or of the outer layer protrudes and forms a part of the meshing of the inner layer and of the outer layer.

4. The endoscope shaft according to claim 1, wherein the structuring layer forms a boundary of the transition region to one of the inner layer or the outer layer of plastic.

5. The endoscope shaft according to claim 3, wherein holes of the structuring layer have a size of over 0.1 mm.

6. The endoscope shaft according to claim 1, wherein the inner layer and the outer layer are meshing together in the transition region in a meandering fashion.

7. The endoscope shaft according to claim 1, wherein the outer layer is enclosed by at least one external layer, and/or the inner layer encloses at least one internal layer.

8. The endoscope shaft according to claim 1, wherein the plastic of the inner layer has a melting point that is at least 30° C. lower than the melting point of the plastic of the outer layer.

9. The endoscope shaft according to claim 1, wherein the plastic of the outer layer is a glycol-modified polycyclohexylene dimethylene terephthalate (PCTG), and the plastic of the inner layer is a polyurethane (PU), a thermoplastic polyurethane (TPU), a styrene block copolymer, and/or a styrene-ethylene-butylene-styrene (SEBS).

10. The endoscope shaft according to claim 3, wherein the structuring layer is formed substantially from metal wires and/or plastic fibers, or from a perforated woven fabric of plastic fibers and/or metal wires.

11. The endoscope shaft according to claim 3, wherein holes of the structuring layer have a size of over 0.2 mm.

12. The endoscope shaft according to claim 3, wherein holes of the structuring layer have a size of over 0.5 mm or 1 mm.

13. The endoscope shaft according to claim 3, wherein the webs of the structuring layer have a width of over 0.1 mm.

14. The endoscope shaft according to claim 3, wherein the webs of the structuring layer have a width of over 0.2 mm or over 0.5 mm.

* * * * *